(12) United States Patent
Ozawa et al.

(10) Patent No.: US 8,834,359 B2
(45) Date of Patent: Sep. 16, 2014

(54) METHOD OF CONTROLLING ENDOSCOPE AND ENDOSCOPE

(75) Inventors: Satoshi Ozawa, Kanagawa (JP); Azuchi Endo, Kanagawa (JP); Akihiko Erikawa, Kanagawa (JP); Takayuki Iida, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 450 days.

(21) Appl. No.: 12/890,136

(22) Filed: Sep. 24, 2010

(65) Prior Publication Data
US 2011/0071352 A1  Mar. 24, 2011

(30) Foreign Application Priority Data

Sep. 24, 2009 (JP) ................. P2009-219242
May 25, 2010 (JP) ................. P2010-119748
Jul. 20, 2010 (JP) ................. P2010-163442

(51) Int. Cl.
*A61B 1/06* (2006.01)
*A61B 1/04* (2006.01)
*G01N 21/00* (2006.01)
*G06K 9/40* (2006.01)
*G06K 9/00* (2006.01)

(52) U.S. Cl.
USPC ........... 600/180; 600/109; 600/178; 600/160; 356/237.1; 382/274; 382/128

(58) Field of Classification Search
CPC .. A61B 1/00009; A61B 1/043; A61B 1/0638; A61B 5/0071
USPC ......... 600/109, 178, 325, 168, 180, 478, 160, 600/476, 328, 317, 473, 310, 443; 362/84, 362/18, 558; 348/71, 68, 65, 70, 46, 45; 607/115, 88; 606/33; 356/237.1; 382/274, 128
See application file for complete search history.

(56) References Cited

U.S. PATENT DOCUMENTS 5,209,220 A   5/1993  Hiyama et al.
5,512,940 A   4/1996  Takasugi et al.
(Continued)

FOREIGN PATENT DOCUMENTS

EP   1 728 464 A1   12/2006
EP   1 795 798 A1    6/2007
(Continued)

OTHER PUBLICATIONS

European Search Report dated Dec. 7, 2010.
(Continued)

*Primary Examiner* — John P Leubecker
*Assistant Examiner* — Ronald D Colque
(74) *Attorney, Agent, or Firm* — McGinn IP Law Group, PLLC

(57) ABSTRACT

An endoscope 100 includes a first light source 45 that emits white illumination light, a second light source 47 that emits narrow-band light and an imaging section that has an imaging device 21 having plural detection pixels and images a region to be observed. The imaging section is caused to output a captured image signal including both a return light component of the white illumination light from the region to be observed by and a return light component of the narrow-band light the white illumination light. From the captured image signal, the return light component of the narrow-band light is selectively extracted, and a brightness level of the extracted return light component of the narrow-band light is changed by changing a light amount of light emitted from the second light source 47.

18 Claims, 11 Drawing Sheets

(56) References Cited

U.S. PATENT DOCUMENTS

| | | | |
|---|---|---|---|
| 5,749,830 A * | 5/1998 | Kaneko et al. | 600/160 |
| 6,293,911 B1 * | 9/2001 | Imaizumi et al. | 600/160 |
| 6,537,211 B1 * | 3/2003 | Wang et al. | 600/178 |
| 7,766,818 B2 * | 8/2010 | Iketani et al. | 600/118 |
| 7,811,229 B2 * | 10/2010 | Sugimoto | 600/160 |
| 7,892,169 B2 | 2/2011 | Gono et al. | |
| 7,907,169 B2 * | 3/2011 | Sugimoto | 348/65 |
| 8,204,287 B2 | 6/2012 | Inoue et al. | |
| 8,216,126 B2 | 7/2012 | Gono | |
| 8,279,275 B2 | 10/2012 | Gono et al. | |
| 8,301,229 B2 | 10/2012 | Gono et al. | |
| 8,337,400 B2 * | 12/2012 | Mizuyoshi | 600/178 |
| 8,506,478 B2 | 8/2013 | Mizuyoshi | |
| 2002/0105505 A1 * | 8/2002 | Sendai | 345/204 |
| 2003/0001104 A1 * | 1/2003 | Sendai et al. | 250/458.1 |
| 2003/0013937 A1 * | 1/2003 | Tsujita et al. | 600/109 |
| 2003/0176768 A1 * | 9/2003 | Gono et al. | 600/109 |
| 2004/0186351 A1 * | 9/2004 | Imaizumi et al. | 600/160 |
| 2005/0054937 A1 * | 3/2005 | Takaoka et al. | 600/476 |
| 2005/0117028 A1 * | 6/2005 | Imaizumi et al. | 348/222.1 |
| 2005/0182321 A1 * | 8/2005 | Frangioni | 600/431 |
| 2006/0020169 A1 * | 1/2006 | Sugimoto | 600/180 |
| 2006/0197831 A1 * | 9/2006 | Takeuchi et al. | 348/70 |
| 2007/0002134 A1 * | 1/2007 | Ishihara et al. | 348/65 |
| 2007/0153542 A1 * | 7/2007 | Gono et al. | 362/574 |
| 2007/0203413 A1 * | 8/2007 | Frangioni | 600/478 |
| 2008/0194972 A1 * | 8/2008 | Gono | 600/476 |
| 2008/0281154 A1 | 11/2008 | Gono et al. | |
| 2008/0294105 A1 * | 11/2008 | Gono et al. | 604/109 |
| 2008/0306338 A1 * | 12/2008 | Yamazaki et al. | 600/109 |
| 2008/0306343 A1 * | 12/2008 | Yamazaki | 600/180 |
| 2009/0023991 A1 | 1/2009 | Gono et al. | |
| 2009/0036741 A1 * | 2/2009 | Igarashi et al. | 600/160 |
| 2009/0040298 A1 | 2/2009 | Yamazaki et al. | |
| 2009/0041319 A1 * | 2/2009 | Yamazaki et al. | 382/128 |
| 2009/0058999 A1 | 3/2009 | Gono et al. | |
| 2009/0065679 A1 * | 3/2009 | Tanimoto | 250/208.1 |
| 2009/0066787 A1 * | 3/2009 | Yamazaki | 348/70 |
| 2009/0082625 A1 * | 3/2009 | Gono | 600/109 |
| 2009/0091614 A1 * | 4/2009 | Gono et al. | 348/68 |
| 2009/0149706 A1 * | 6/2009 | Yamazaki et al. | 600/109 |
| 2009/0190371 A1 * | 7/2009 | Root et al. | 362/554 |
| 2009/0306478 A1 * | 12/2009 | Mizuyoshi | 600/178 |
| 2009/0312607 A1 * | 12/2009 | Sunagawa et al. | 600/160 |
| 2010/0137682 A1 * | 6/2010 | Doguchi et al. | 600/109 |
| 2010/0168588 A1 * | 7/2010 | Matsumoto et al. | 600/478 |
| 2010/0262017 A1 * | 10/2010 | Frangioni | 600/476 |
| 2011/0237895 A1 * | 9/2011 | Yoshida et al. | 600/180 |

FOREIGN PATENT DOCUMENTS

| | | | |
|---|---|---|---|
| EP | 1 880 657 A1 | 1/2008 | |
| EP | 2008 573 A1 | 12/2008 | |
| EP | 2008573 A1 * | 12/2008 | A61B 1/00 |
| JP | 2002-34893 A | 2/2002 | |
| JP | 2005-198794 A | 7/2005 | |
| JP | 2006-346196 A | 12/2006 | |
| JP | 2008-307294 A | 12/2008 | |
| JP | 2009-142415 A | 7/2009 | |
| WO | WO 2007/123028 A1 | 11/2007 | |
| WO | WO 2007123028 A1 * | 11/2007 | |

OTHER PUBLICATIONS

U.S. Appl. No. 12/890,357 (29 pages of specification and 11 sheets of drawings for Figures 1-12).
U.S. Office Action dated Oct. 1, 2012 for U.S. Appl. No. 12/890,357.
Office Action dated Apr. 10, 2013 in U.S. Appl. No. 12/890,357.
Office Action dated Nov. 25, 2013 in U.S. Appl. No. 12/890,357.
Japanese Office Action dated Oct. 15, 2013 with partial English translation thereof.
Japanese Office Action dated Jun. 17, 2014 with a partial English translation.
United States office Action dated Jun. 27, 2014 in co-pending U.S. Appl. No. 12/890,357.

* cited by examiner

White light observation image

Narrow-band light observation image

METHOD OF CONTROLLING ENDOSCOPE AND ENDOSCOPE

CROSS-REFERENCE TO RELATED APPLICATIONS

This application claims the benefit of Japanese Patent Application No. 2009-219241 (filed Sep. 24, 2009), No. 2010-146866 (filed Jun. 28, 2010), and No. 2010-163443 (filed Jul. 20, 2010), the entire contents of which are hereby incorporated by reference, the same as if set forth at length.

BACKGROUND OF THE INVENTION

1. Technical Field

The present invention relates to a method of controlling an endoscope and an endoscope.

2. Description of the Related Art

Recently, an endoscope is used which applies narrow-band light in a specific narrow wavelength band to biological mucosa tissue to obtain tissue information at a desired depth of the body tissue, i.e., perform a so-called special light observation (see JP 2002-34893 A (corresponding to US 2003/0176768 A, US 2008/0281154 A and US 2008/0294105 A))). In such an endoscope, it is possible to easily visualize body information, which cannot be obtained in a normal observation image, such as microstructure of a new blood vessel generated in a mucosa layer or submucosa layer and enhancement of a lesion part. For example, for a cancer lesion part that is an object to be observed, when blue narrow-band light is applied to the mucosa tissue, it is possible to observe micro blood vessels or microstructure of superficial layer more specifically. Therefore, it is possible to diagnose the lesion part more exactly.

However, in the special light observation, the observation is performed with a captured image that is obtained when the narrow-band light is applied to the body tissue. Hence, even when an intensity of illumination of the narrow-band light is appropriately adjusted at the observation time in a closeup view, it is not possible to obtain an intensity of illumination enough to observe the superficial blood vessels at the observation time in a distant view having a wide angle of view. Due to this, a gain of an imaging section or a display section is adjusted whenever observation conditions such as an observation object or an observation position is changed, thereby enabling the observation to be performed with a proper brightness level. Additionally, in the endoscope of JP 2002-34893 A, the light from a white light source is changed in a time division manner by a color filter, and light (R light, G light, B light) in different wavelength bands are frame-sequentially emitted to perform an imaging. Due to this, in order to obtain an observation image of full colors in real time, it is necessary to combined captured images of plural frames (R frame, G frame, B frame), so that it is difficult to increase a frame rate of the observation image.

SUMMARY OF THE INVENTION

One embodiment of the invention provides a method of controlling an endoscope that always generates an observation image by narrow-band light having a proper brightness level even when observation conditions such as observation object and an observation position are changed in performing a special light observation by an endoscope and that enables body information obtained by the narrow-band light to be clearly observed, and an endoscope.

One embodiment of the invention has the following configuration.

(1) A method controls an amount of illumination light of an endoscope. The endoscope includes a first light source, a second light source and an imaging section. The first light source emits white illumination light. The second light source that emits narrow-band light having a wavelength band narrower than that of the white illumination light. The imaging section images a region to be observed by an imaging device having a plurality of detection pixels. The method includes: causing the imaging section to output a captured image signal including both of a return light component of the white illumination light from the region to be observed and a return light component of the narrow-band light from the region to be observed; and selectively extracting the return light component of the narrow-band light from the captured image signal; and changing an amount of the narrow-band light emitted from the second light source to change a brightness level of the extracted return light component of the narrow-band light.

(2) An endoscope includes a first light source, a second light source, an imaging section and a controller. The first light source emits white illumination light. The second light source emits narrow-band light of a wavelength band narrower than the white illumination light. The imaging section includes an imaging device having a plurality of detection pixels. The imaging section outputs a captured image signal. The controller changes an amount of light emitted from the second light source, based on the control method of (1).

With the above method of controlling the endoscope, even if the observation conditions such as an observation object and an observation position are changed in performing the special light observation with the endoscope, it is possible to always generate an observation image by the narrow-band light having a proper brightness level and to clearly observe the body information obtained by the narrow-band light.

DETAILED DESCRIPTIONS OF EXEMPLARY EMBODIMENTS

Hereinafter, exemplary embodiments of the invention will be specifically described with reference to the accompanying drawings.

Figure 1:
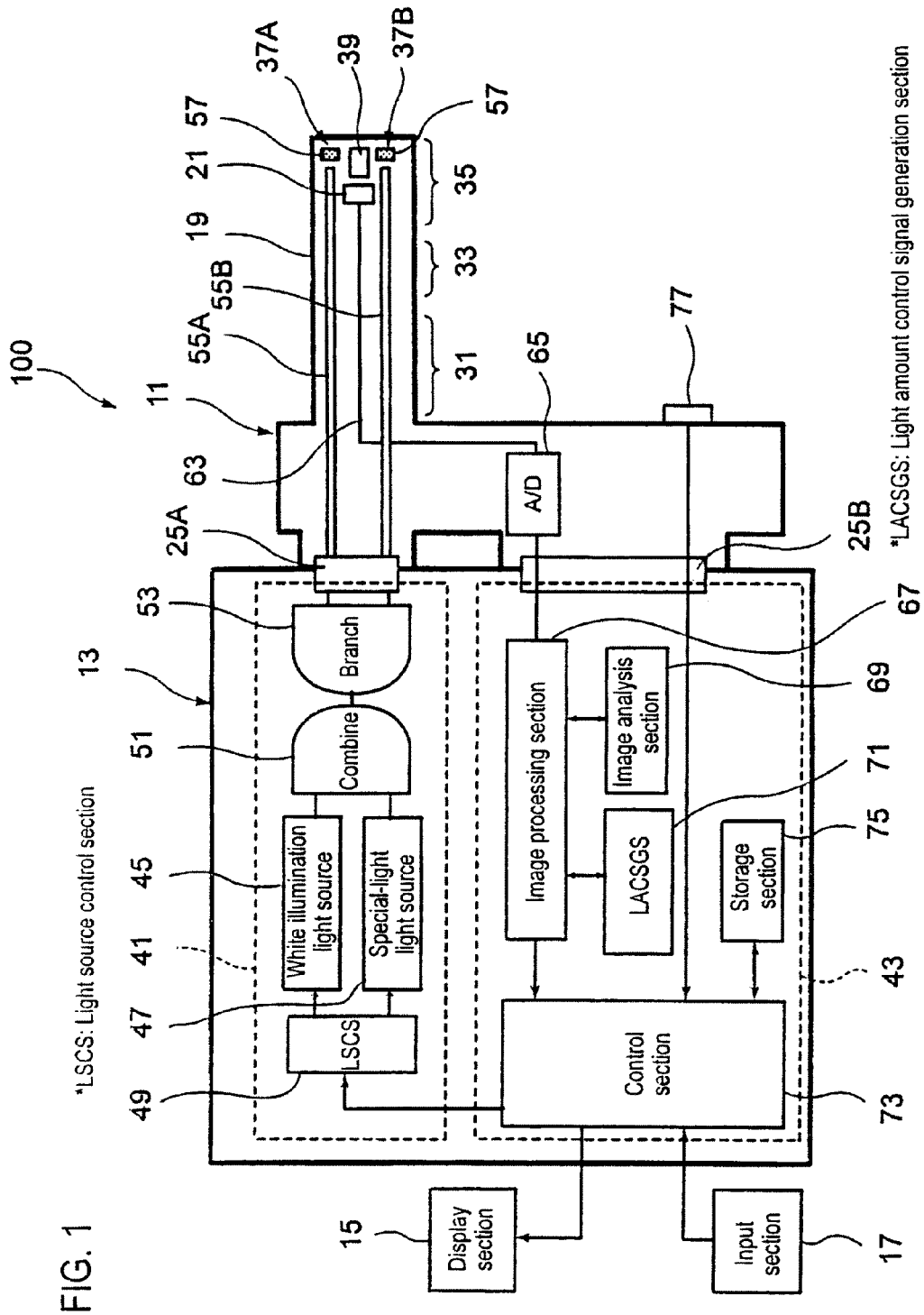
FIG. 1 is a view illustrating an exemplary embodiment of the invention and is a conceptual block diagram of an endoscope.
Figure 2:
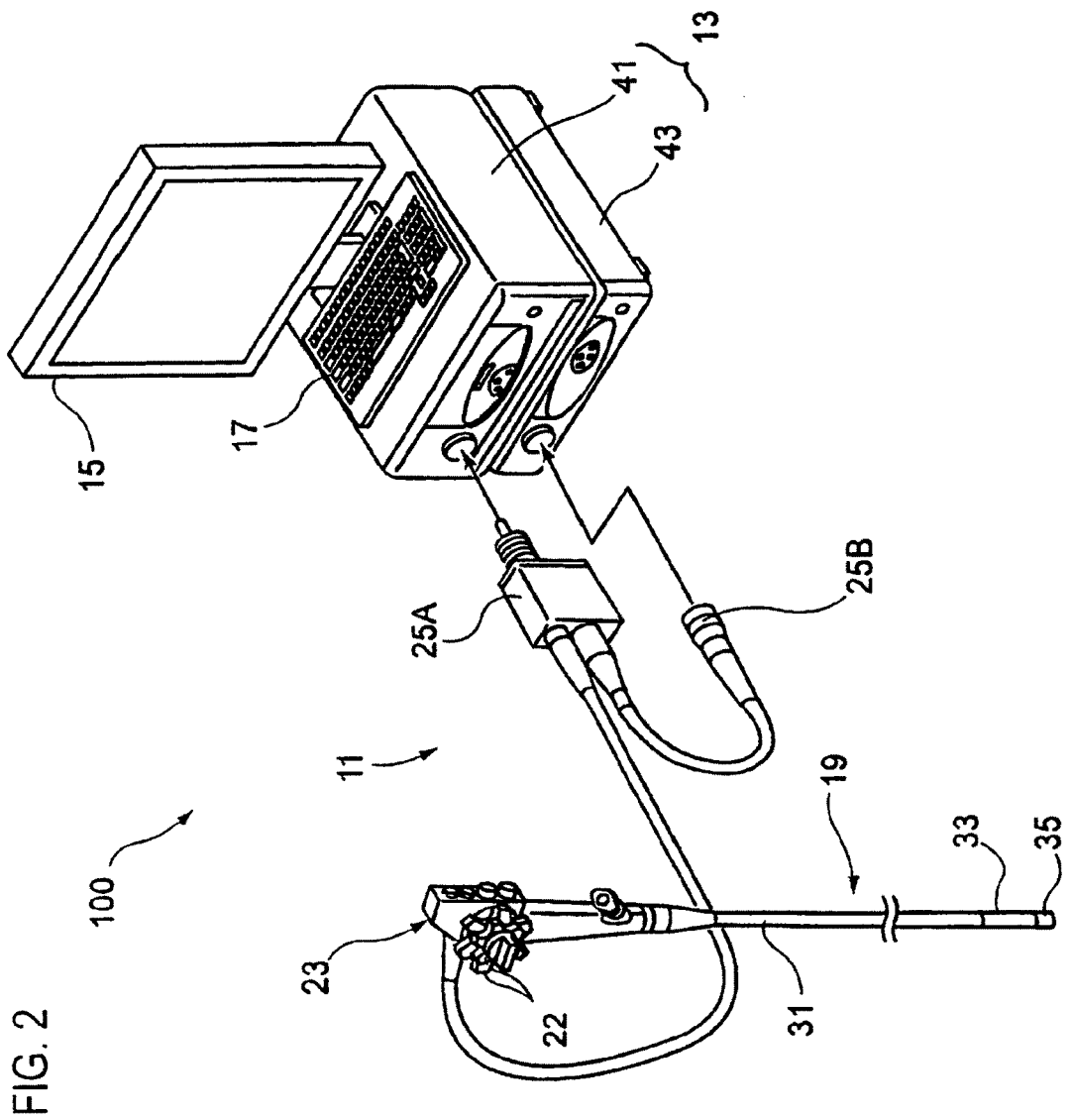
FIG. 2 is an appearance view of an example of the endoscope shown in FIG. 1.

FIG. 1 is a view illustrating an exemplary embodiment of the invention and is a conceptual block diagram of an endoscope. FIG. 2 is an appearance view of an example of the endoscope shown in FIG. 1.

As shown in FIGS. 1 and 2, an endoscope 100 includes an endoscope 11, a control apparatus 13 to which the endoscope 11 is connected, a display section 15 that is connected to the control apparatus 13 and displays image information, and an input section 17 that receives an input operation. The endoscope 11 is an electronic endoscope having an illumination optical system that emits illumination light from a leading end of an endoscope insertion part 19, which is inserted into an object to be examined, and an imaging optical system including an imaging device 21 (see FIG. 1) that has detection pixels of plural colors and captures a region to be observed.

The endoscope 11 has the endoscope insertion part 19, an operation section 23 (see FIG. 2) that performs a bending operation of the leading end of the endoscope insertion part 19 and an observation operation, and connector sections 25A, 25B enabling the endoscope 11 to be detachably connected to the control apparatus 13. Although not shown, various channels such as a forceps channel for inserting a treatment tool for collecting tissue and an air supply/water supply channel are provided in the operation section 23 and the endoscope insertion part 19.

The endoscope insertion part 19 has a flexible part 31 having flexibility, a bending part 33 and a leading end part (hereinafter, referred to as endoscope leading end part) 35. As shown in FIG. 1, the endoscope leading end part 35 has irradiation ports 37A, 37B through which light is applied to a region to be observed, and an imaging device 21 that obtains image information of the region to be observed, such as CCD (Charge Coupled Device) type image sensor or CMOS (Complementary Metal-Oxide Semiconductor) type image sensor. In addition, in front of a light-receiving surface of the imaging device 21, an object lens unit 39 is arranged. When a CCD type image sensor is used, it is possible to obtain a captured image having low noise and less image distortion because of the global shutter of the CCD sensor.

The bending part 33 is provided between the flexible part 31 and the leading end part 35, and can be bent by a rotation operation of an angle knob 22 disposed in the operation section 23 shown in FIG. 2. The bending part 33 can be bent in arbitrary direction and arbitrary angle, depending on parts of an object to be examined for which the endoscope 11 is used, thereby enabling observation directions of the irradiation ports 37A, 37B and imaging device 21 of the endoscope leading end part 35 to be directed toward a desired observation part. In addition, although not shown, the irradiation ports 37A, 37B of the endoscope insertion part 19 are provided with a cover glass or lens.

The control apparatus 13 has a light source device 41 that generates illumination light to be supplied to the irradiation ports 37A, 37B of the endoscope leading end part 35, and a processor 43 that executes image processing for a captured image signal from the imaging device 21. The control apparatus 13 is connected to the endoscope 11 via the connector sections 25A, 25B. In addition, the processor 43 is connected with the display section 15 and the input section 17. The processor 43 executes the image processing for the captured image signal transmitted from the endoscope 11, based on a command from the operation section 23 or input section 17 of the endoscope 11, and generates and supplies images to the display section 15 for display.

The light source device 41 has a blue laser light source (white illumination light source) 45 having a center wavelength of 445 nm and a purple laser light source (special light source) 47 having a center wavelength of 405 nm, as light emitting sources. The light emitted from the semiconductor light emitting devices of the respective light sources 45, 47 are individually controlled by a light source control section 49, so that a light amount ratio of the light emitted from the blue laser light source 45 and the light emitted from the purple laser light source 47 can be changed.

Examples of the blue laser light source 45 and the purple laser light source 47 include InGaN-based laser diodes of a broad area type. Alternatively, InGaNAs-based diodes or GaNAs-based diodes may be also used. Additionally, a light emitting element such as light emitting diode may be used for the light sources.

The laser light emitted from the respective light sources 45, 47 are respectively input to optical fibers by condenser lenses (not shown) and are transmitted to the connector section 25A via a combiner 51, which is an optical multiplexer, and a coupler 53, which is an optical demultiplexer. It is noted that the invention is not limited thereto. For example, the laser light from the respective light sources 45, 47 may be directly transmitted to the connector section 25A without using the combiner 51 and the coupler 53.

The laser light, which are transmitted to the connector section 25A after the blue laser light having the center wavelength of 445 nm and the purple laser light source having the center wavelength of 405 nm are combined, are transmitted to the endoscope leading end part 35 of the endoscope 11 by optical fibers 55A, 55B, respectively. The blue laser light excites fluorescent materials 57, which are an example of wavelength conversion members disposed at light emitting ends of the optical fibers 55A, 55B of the endoscope leading end part 35, thereby emitting fluorescence. In addition, a part of the blue laser light passes through the fluorescent materials 57, as it is. The purple laser light passes through the fluorescent materials 57 without exciting the fluorescent materials 57, so that it becomes illumination light of a narrow-band wavelength.

The optical fibers 55A, 55B are multimode fibers. As the fibers, a thin fiber cable having a core diameter of 105 μm, a clad diameter of 125 μm and a diameter φ of 0.3 to 0.5 mm, which includes a protective layer that is an outer cover, may be used, for example.

The fluorescent materials 57 include plural fluorescent materials (for example, YAG-based fluorescent materials or fluorescent materials of BAM ($BaMgAl_{10}O_{17}$)) that absorb a part of the blue laser light to excitedly emit light of green to yellow. Thereby, the light of green to yellow, which are obtained by the excitation light of the blue laser light, and the blue laser light, which passes through the fluorescent materials 57 without being absorbed by the fluorescent materials 57, are combined to constitute white (pseudo-white) illumination light. As this exemplary embodiment, when the semiconductor light emitting devices are used as the excitation light sources, it is possible to obtain the white light of high intensity in a high light emitting efficiency, to easily adjust an intensity of the white light and to suppress changes in color temperatures and chromaticity of the white light.

The fluorescent materials 57 can prevent noise superposition, which is an obstacle to the imaging, or flicker that is generated when displaying a moving picture, which are caused due to speckles generated by coherence of the laser lights. In addition, the fluorescent material 57 is preferably made of material in which light of an infrared region is little absorbed and highly scattered, taking into consideration a difference of refractive indices between a fluorescent substance constituting the fluorescent material and a resin for fixing and solidification becoming a filler. Thereby, it is possible to increase a scattering effect without decreasing the intensity of light of red or infrared region, so that an optical loss is reduced.

Figure 3:
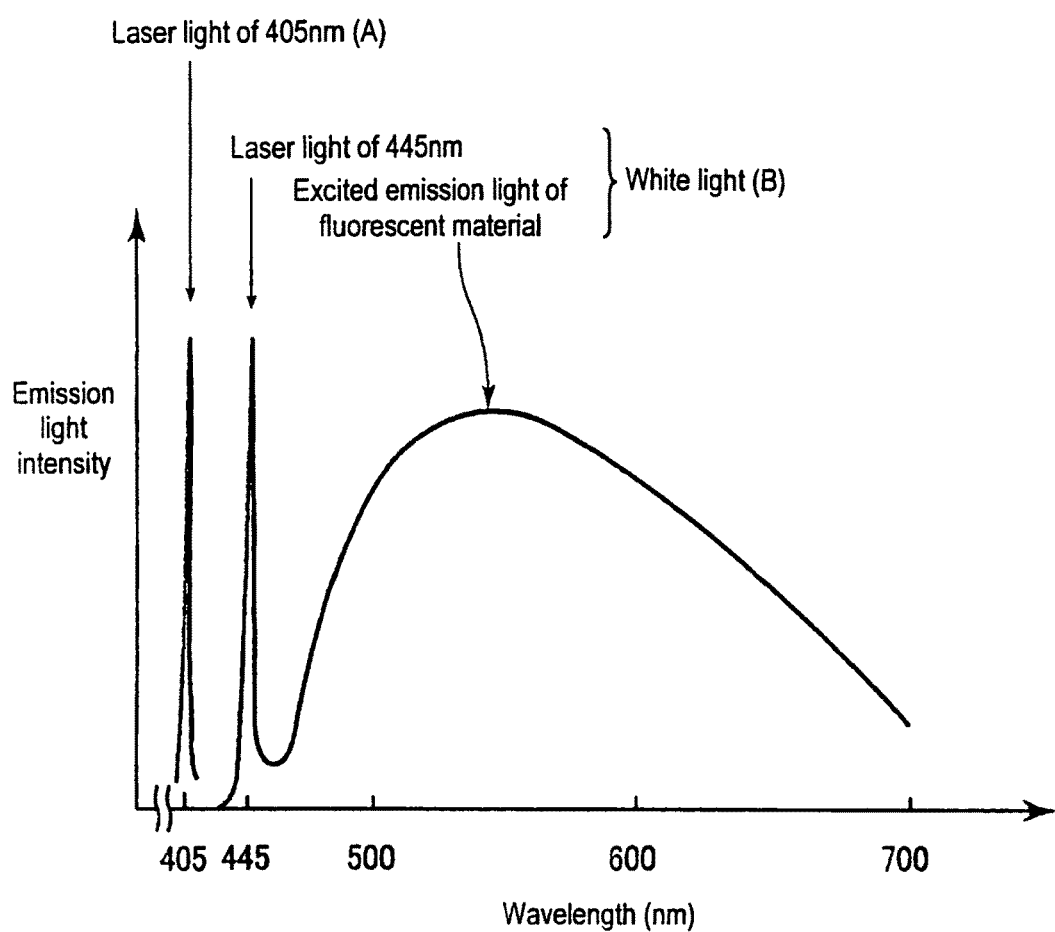
FIG. 3 is a graph showing spectra of purple laser light from a purple laser light source and blue laser light from a blue laser light source and emission spectrum which is obtained by wavelength-converting the blue laser light by a fluorescent material.

FIG. 3 is a graph showing spectra of the purple laser light from the purple laser light source 47 and blue laser light from the blue laser light source 45 and emission spectrum which is obtained by wavelength-converting the blue laser light by the fluorescent materials 57. The purple laser light is indicated with an emission line having a center wavelength of 405 nm (profile A). Also, the blue laser light is indicated with an emission line having a center wavelength of 445 nm. The excited emission light from the fluorescent materials 57 by the blue laser light forms a spectral intensity distribution in which luminescence intensity is increased in a wavelength band of about 450 nm to 700 nm. The white light is formed by the profile B of the excited emission light and blue laser light.

The white light described in the specification is not strictly limited to the light including all wavelength components of the visible lights. For example, the white light may include light of specific wavelength bands such as R (red), G (green) and B (blue) that are reference colors. For example, the white light may include light including wavelength components from green to red or light including wavelength components from blue to green, in a broad sense.

In the endoscope 100, it is possible to relatively increase or decrease the luminescence intensities of the profiles A and B by the light source control section 49 and to thus generate illumination light having any brightness balance.

Referring to FIG. 1, as described above, the illumination light including the white light, which is formed by the blue laser light and the excited emission light from the fluorescent materials 57, and the narrow-band light by the purple laser light is applied toward a region to be observed of an object to be examined from the leading end part 35 of the endoscope 11. An image of the region to be observed to which the illumination light is applied is formed on the light receiving surface of the imaging device 21 by the object lens unit 39 and captured.

A captured image signal output from the imaging device 21 after the imaging is transmitted to an A/D converter 65 through a scope cable 63, which is then converted into a digital signal. The converted signal is input to an image processing section 67 of the processor 43 through the connector section 25B. The image processing section 67 converts the input digital image signal to image data and outputs, to a control section 73, desired output image information and a control signal for the light source control section 49, in cooperation with an image analysis section 69 and a light amount control signal generation section 71, which will be specifically described below.

The output image information which is input to the control section 73 is displayed on the display section 15 as an endoscope observation image, and is stored in a storage section 75 having a memory or a storage device, if necessary. In addition, the endoscope 11 includes a mode switching button 77 which will be described in detail below, and a switching signal from the mode switching button 77 is input to the control section 73.

Figure 4:
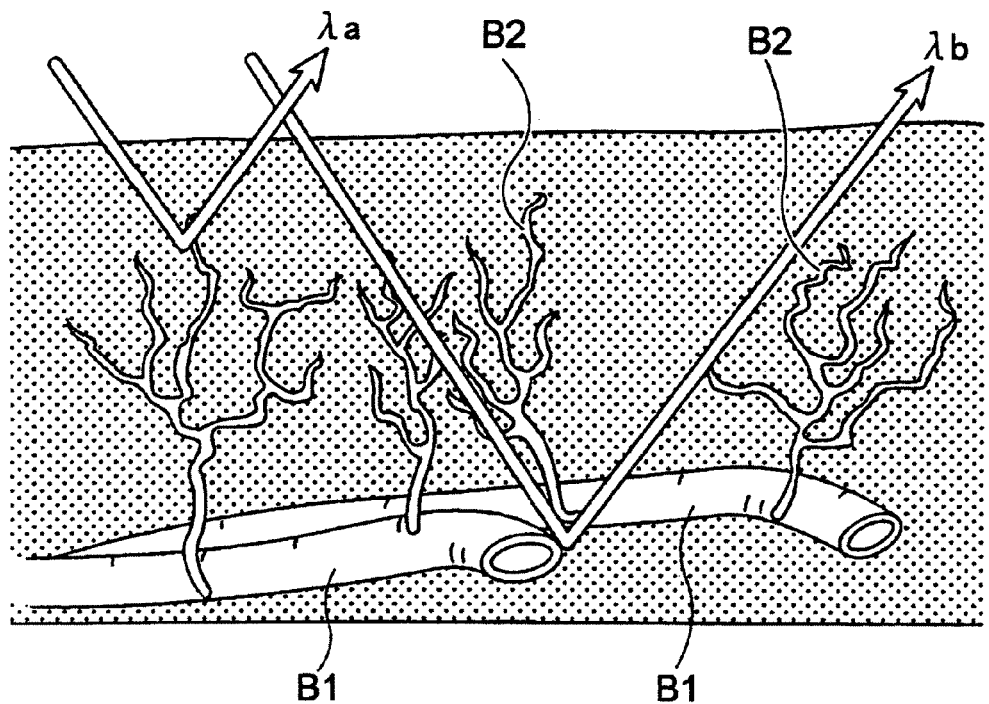
FIG. 4 schematically shows blood vessels in mucosal surface of body tissue.

FIG. 4 schematically shows blood vessels in mucosal surface of body tissue. The mucosal surface of body tissue is reported in which capillary vessels B2 such as dendritic vascular network are formed to extend from blood vessels B1 of deep mucosa to the mucosal surface, and it has been reported that the lesions of the body tissue are exhibited in the microstructure of the capillary vessels B2. Accordingly, when performing an endoscope diagnosis, it is attempted to find a micro lesion in early stage or to diagnose a range of lesions by emphasizing an image of the capillary vessels of the mucosal surface with the narrow-band light of visible short wavelengths of blue to purple.

When the illumination light is incident into the body tissue, the illumination light is diffusively spread in the body tissue. The absorption and scattering properties of the body tissue depends on wavelengths, and the scattering property is stronger as the wavelength is shorter. In other words, a degree of light reaching a deep position is changed depending on the wavelengths of the illumination light. When the illumination light is in a wavelength band $\lambda a$ of about 400 nm, the blood vessel information is obtained from the capillary vessels in the mucosal surface. When the illumination light is in a wavelength band $\lambda b$ of about 500 nm, the blood vessel information including blood vessels in the deeper layer is obtained. Due to this, when the blood vessels in the body tissue is observed, a light source having a center wavelength of 360 to 800 nm, preferably 365 to 515 nm is used. In particular, when the superficial blood vessels are observed, a light source having a center wavelength of 360 to 470 nm, preferably 360 to 450 nm is used.

Figure 5:
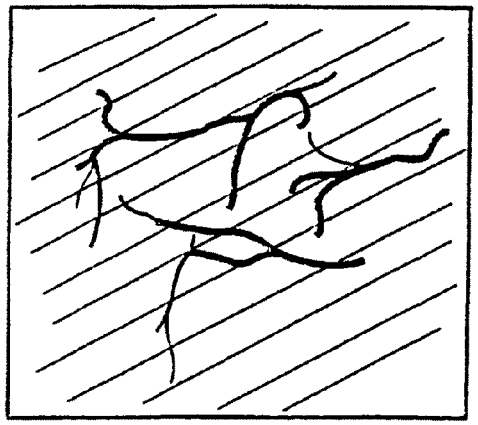
FIG. 5 is a schematic example of an observation image that is displayed by an endoscope and is an explanatory view showing a white light observation image and a narrow-band light observation image.
Figure 5:
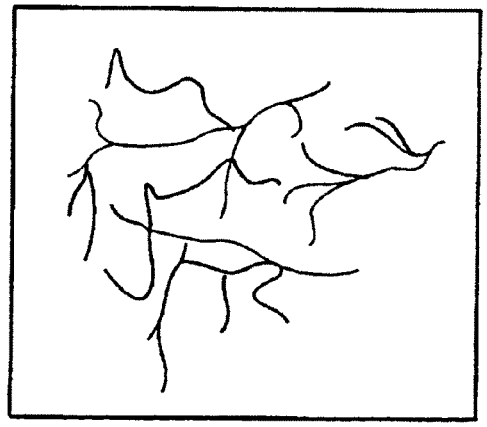

FIG. 5 is an example of an observation image by the endoscope. For a white light observation image which is obtained when the white light is used as the illumination light, a blood vessel image of the relatively deep mucosa is obtained, and the brightness of the entire image can be easily enhanced. In the meantime, for a narrow-band light observation image which is obtained when the narrow-band light including many visible short wavelength components is used as the illumination light, it is possible to clearly see the micro capillary vessels in the mucosal surface.

If the observation image by the white light and the observation image by the narrow-band light are combined, it is possible to secure the sufficient brightness for the entire image and to obtain an observation image in which the capillary vessels in the mucosal surface of the body tissue are enhanced and an affected area can be thus easily diagnosed. Accordingly, in the endoscope 100 of this exemplary embodiment, the narrow-band light of the profile A and the white light of the profile B shown in FIG. 3 are individually emitted from the endoscope leading end part 35 and the amount of the light thereof is continuously controlled. Also, the amount of the light is controlled so that the light components of the both illumination light are included in one frame of the imaging frames by the imaging device 21. In other words, a captured image, which is obtained by imaging a region to be observed to which both the white light and the narrow-band light are applied in an arbitrary light amount ratio, becomes an observation image.

By independently controlling the amount of the white light and the amount of the narrow-band light, it is possible to emphasize or blur only the imaging information by the narrow-band light in the observation image and to generate an observation image. Thus, the observation images by the both light are appropriately combined without the observation image by the narrow-band light being hidden by the observation image by the white light. Thereby, it is possible to obtain an observation image suitable for an endoscope diagnosis, which enables the micro blood vessel structure to be easily examined by emphasizing the superficial blood vessels by the narrow-band light, while brightly illuminating the entire surrounding of the observation part with the white light.

Figure 6:
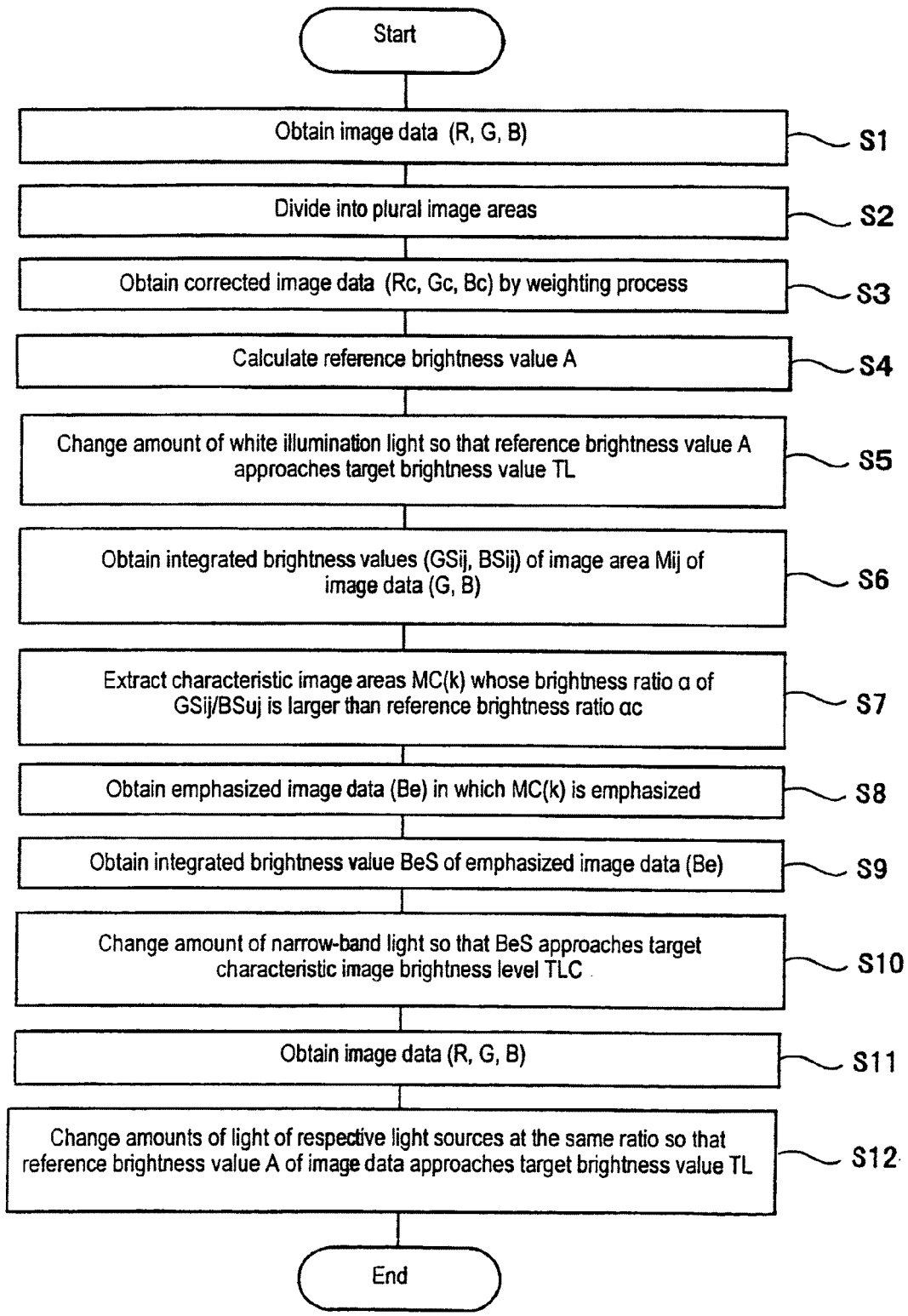
FIG. 6 is a flow chart showing a sequence of controlling a brightness level of an image signal when images are captured with a white illumination light source and a special light source.

Next, based on a flow chart of FIG. 6, it will be described a sequence of controlling a ratio of the amount of light emitted from the blue laser light source 45 which is a white illumination light source and the amount of the purple laser light source 47 which is a special light source so as to properly maintain an average brightness of the entire captured image and a mixing balance of the image by the narrow-band light and the image by the white light, when performing the imaging with the illumination light in which the white light is added to the narrow-band light.

Figure 7A:
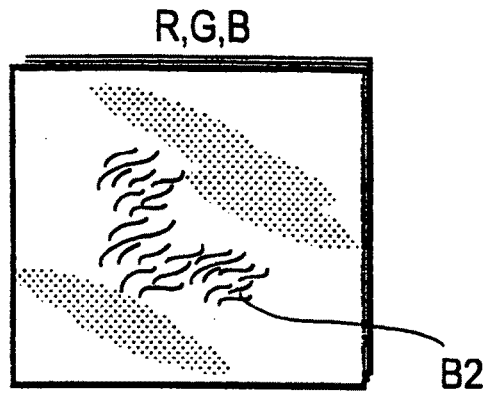
FIG. 7A illustrates an example of captured image data.

First, in a state where both the blue laser light source 45 and the purple laser light source 47 shown in FIG. 1 are turned on to apply the narrow-band light and the white light to a region to be observed, the region to be observed is imaged by the imaging device 21. A resultantly obtained captured image signal is input to the image processing section 67, so that each captured image (R, B) having a predetermined tone expression width as shown in FIG. 7A is obtained (S1). The respective captured images (R, G, B) constitute image information which is obtained at the same imaging timing.

When the imaging device 21 is an imaging device of a primary color system, detection levels of R, G and B that are detection colors are treated as brightness values of the reference colors (R, G, B). However, when the imaging device is an imaging device of a complementary color system, detection levels of three colors of C (cyan), M (magenta) and Y (yellow) which are detection colors or four colors of C, M, Y and G which are detection colors are calculated and converted into brightness values of the reference colors of R, G and B.

In the meantime, the conversion of CMY or CMYG into RGB is performed by the image processing section 67, based on a predetermined calculation equation or table. In other words, the captured images (C, M, Y) or captured image (C, M, Y, G) which has been subjected to the A/D conversion are converted into signals of captured images (R, G, B) of the respective reference colors. The blue component of the shortest wavelength of the captures images (R, G, B) of the respective reference colors includes information of the superficial blood vessels B2 (see FIG. 4), which is obtained by the narrow-band light having the center wavelength of 405 nm.

Figure 7B:
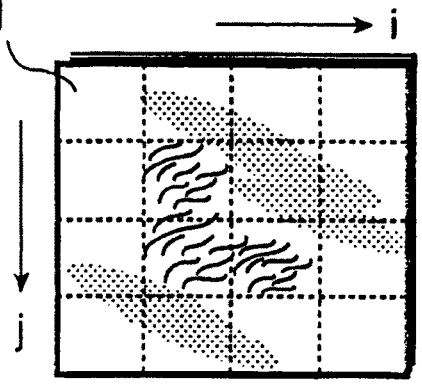
FIG. 7B illustrates the image data which is divided into image areas.

The image processing section 67 divides the captured images (R, G, B) of the respective reference colors into arbitrary number of image areas Mij, as shown in FIG. 7B (S2). In the shown example, the captured images (R, G, B) are commonly divided into 16 (4×4) image areas in total (Mij: I=0 to 3, j=0 to 3). In the meantime, the division number of the image areas may be arbitrary.

Figure 7C:
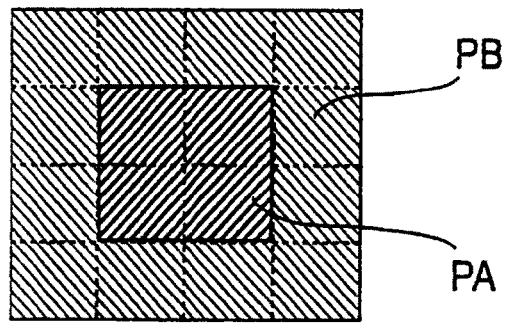
FIG. 7C illustrates a weighting process which is executed according to screen positions.
Figure 7D:
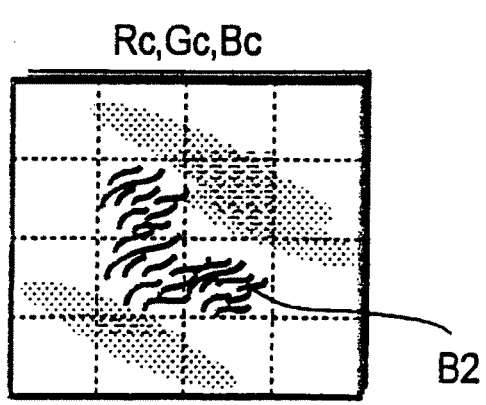
FIG. 7D illustrates corrected image data which has been subjected to the weighting-process.

Next, with regard to the respective divided captured images (R, G, B), the image analysis section 69 performs a weighting process for each image area Mij to obtain corrected image data Rc, Gc, Bc (S3). As shown in FIG. 7C, the weighting process is a process of emphasizing image area PA in a screen center of each captured images (R, G, B), compared to an image area PB of a screen surrounding, particularly a process of emphasizing an observation object displayed on the screen center to be carefully watched. The brightness value of each captured image is corrected by a matrix calculation using a correction matrix. In the corrected image data (Rc, Gc, Bc) in which the screen centers of the captured images (R, G, B) are weighted, the information of the capillary vessels B2 of the superficial layer, which is a main observation object, is emphasized, as shown in FIG. 7D.

Next, the image analysis section 69 calculates a reference brightness value A that indicates brightness of the entire image of the corrected image data (Rc, Gc, Bc) (S4). The reference brightness value A is an index obtained by averaging the brightness values of respective pixels of the corrected image data (Rc, Gc, Bc) for all pixels (N pixels), as shown in an equation (1).

$$A = \frac{\sum_N Rc + \sum_N Gc + \sum_N Bc}{3N} \quad (1)$$

The control section 73 changes the light amount of the white illumination light so that the reference brightness value A obtained from the corrected image data (Rc, Gc, Bc) approaches a predetermined target brightness level TL1 (S5). In other words, the image processing section 67 compares the reference brightness value A, which is obtained by the image analysis section 69, with the target brightness level TL, which is stored in the storage section 75 in advance, and causes the light amount control signal generation section 71 to generate a control signal to increase or decrease (change) the light amount of the light emitted from the blue laser light source 47 so that the reference brightness value A approaches the target brightness level TL.

The generated control signal is transmitted to the light source control section 49 via the control section 73, and the light source control section 49 controls the light amount of light emitted from the blue laser light source 47, based on the input control signal. Thereby, when the reference brightness value A is less than the target brightness level TL, the light amount of the white illumination light is increased, and when the reference brightness value A exceeds the target brightness level TL, the light amount of the white illumination light is decreased.

Next, the image processing section 67 calculates integrated brightness values GSij, BSij of the respective pixels in the respective divided image areas Mij of the captured images (G, B) obtained in S1 (S6). In other words, the image processing section calculates the integrated brightness values GSij, BSij for each of the total of 16 image areas Mij of the captured images (G, B).

Then, the image processing section calculates a brightness ratio α, which is a ratio of the integrated brightness value GSij to the integrated brightness value BSij, in the image areas Mij having a same relation in image position to each other, based on an equation (2). The image processing section 67 extracts an image area(s) having the brightness ratio α which greater than a reference brightness ratio αc, which is a predetermined threshold value, as a characteristic image area MC(k).

$$\alpha = \frac{GS_{i,j}}{BS_{i,j}} \quad (2)$$

Figure 8A:
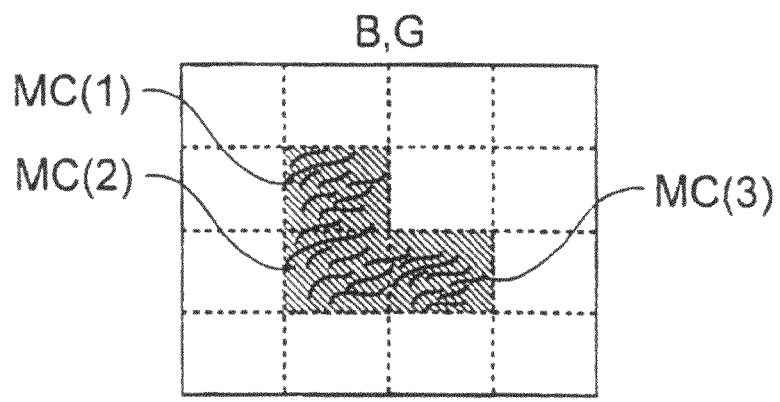
FIG. 8A illustrates characteristic image areas which are extracted from the image data.

FIG. 8A shows the characteristic images areas MC(k) extracted from the captured images (B, G) (for example, three image areas: k=1, 2, 3).

Figure 8B:
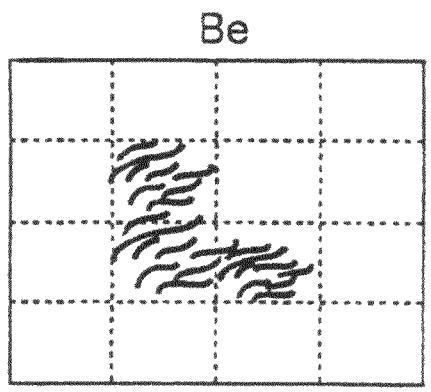
FIG. 8B illustrates emphasized image data.

Next, for the captured image (B) including much information about the capillary vessels B in the superficial layer emphasized by the narrow-band light having the center wavelength of 405 nm, the image processing section 67 emphasizes the respective pixels of the extracted characteristic image areas MC(k) by the weighting process, thereby obtaining blue emphasized image data (Be) as shown in FIG. 8B (S8). The emphasized image data (Be) is an image obtained by emphasizing the characteristic image areas MC(k) only. In the shown example, the image areas in which the capillary vessels B are displayed are emphasized so that its brightness is greater than the other image areas.

Then, the image processing section 67 calculates integrated brightness value BeS for the entire screen, based on an equation (3).

$$BeS = \sum_N Be \quad (3)$$

Here, the control section 73 causes the light amount control signal generation section 71 to generate a control signal to increases or decreases (change) the light amount of light emitted from the purple laser light source 47, so that the obtained integrated brightness value BeS approaches a predetermined target characteristic image brightness level TLc. The control signal is input to the light source control section 47 through the control section 73. Then, when the integrated brightness value BeS is less than the target characteristic image brightness level TLc, the light source control section 49 increases the light amount of light emitted from the purple laser light source 47, and when the integrated brightness value BeS exceeds the target characteristic image brightness level TLc, the light source control section decreases the light amount of light emitted from the purple laser light source 47 (S10).

Figure 8C:
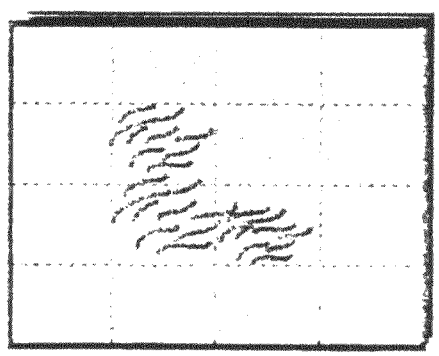
FIG. 8C illustrates the captured images after brightness levels thereof are adjusted.

After the light amount of light emitted from the purple laser light source 47 is adjusted, a captured image signal is obtained by the imaging device 21, so that respective captured images (Ra, Ga, Ba) are generated (S11). Then, the reference brightness value A of the captured images (Ra, Ga, Ba) is calculated by the weighting process for each image area and the equation (1). An example of the captured images (Ra, Ga, Ba) is shown in FIG. 8C. If the reference brightness value A exceeds the target brightness level TL, for example, if the brightness level of the captured image exceeds a maximum tone expression width as a result of the adjustment of the amount of the emitted light, it is necessary to correct. Therefore, if the reference brightness value A exceeds the target brightness level TL, the amounts of light emitted from the blue laser light source 45 and the purple laser light source 47 are decreased in a same ratio so that the reference brightness value A becomes the target brightness level TL (S12).

Figure 8D:
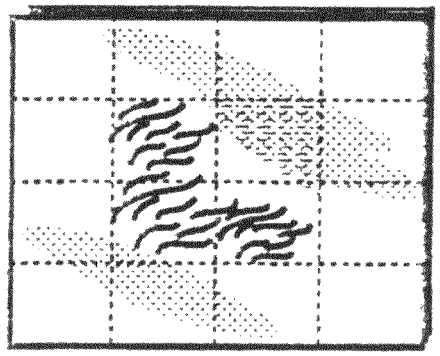
FIG. 8D illustrates an image which is adjusted to have a target brightness level.

Thereby, as shown in FIG. 8D, an observation image is obtained in which both the image information by the white light and the image information by the narrow-band light, which is controlled to have a desired brightness level, are made to have proper brightness levels for the entire screen.

As described above, the imaging is performed by emitting the narrow-band light and the white light at the same time, so that it is possible to emphasize and display the superficial blood vessels by the narrow-band light while securing the brightness of the observation image by the white light. In other words, the imaging is performed by emitting the light from both the white illumination light source for normal observation and the special light source for special observation. As a result, the obtained observation image becomes an image in which an object (for example, superficial blood vessels and glands), which is intended to be observed by the narrow-band light, is made to have an optimal brightness level and the brightness value is not saturated for the entire image, i.e., the maximum tone expression width is not exceeded. Thereby, it is possible to always display an observation object having a proper brightness level and to clearly display an observation part, which is emphasized by the narrow-band light, without being hidden by the white light. Accordingly, it is possible to easily obtain an endoscope observation image, which can contribute to an early finding of a lesion part, without an operator's adjustment operation.

With the observation image, it is possible to observe a detailed structure of the superficial layer emphasized by the narrow-band light in real time while seeing the entire structure of the observation part by the white illumination light. Hence, by increasing a tracking property to movement of an observation object at a high frame rate, with regard to the cancer lesion in which a density of the micro blood vessels is increased compared to a normal part, for example, it is possible to diagnose the superficial micro blood vessels or microstructure quickly and accurately while comparing them with the surroundings of the lesion part.

In the meantime, although the blue laser light source 45 and the purple laser light source 47 are turned on at the same time to perform the imaging, it may be possible to alternately turn on the light sources 45 and 47 within a light receiving time period in one frame of the imaging device. In this case, it is possible to save the power and suppress the heat generation.

Also, the brightness level control of the captured image signal is switched between ON and OFF by pushing the mode switching button 77 (see FIG. 1). In the case of the ON state, the special light observation mode is made effective, so that it is possible to perform the observation by the white light illumination and the narrow-band light at the same time. In the case of the OFF state, the normal observation mode is made effective, so that it is possible to change the light amount of light emitted from the purple laser light source 47 in the same ratio as the light amount of light emitted from the blue laser light source 45. In this manner, it is possible to improve the usability of the endoscope by selectively switching between the special light observation mode and the normal observation mode.

Furthermore, the observation object by the narrow-band light may be autofluorescence or drug fluorescence from the body tissue, in addition to the superficial capillary vessels or micro mucosa shape of the body tissue. Also, the intensity of the return light from the region to be observed may be appropriately changed into a state suitable for diagnosis.

Figure 9:
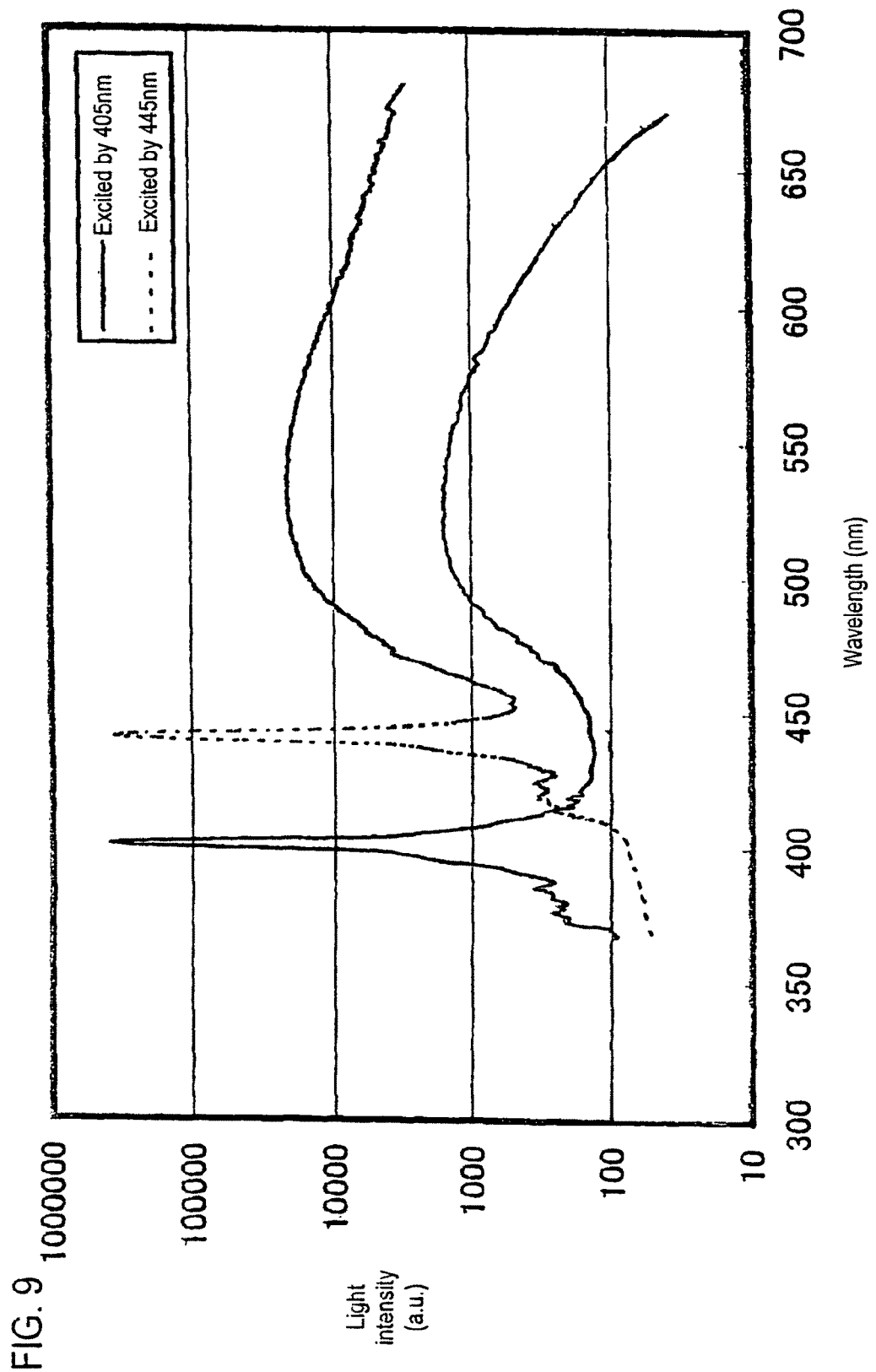
FIG. 9 shows another example of emission spectra of illumination light by a white illumination light source, a special light source and a fluorescent material.

FIG. 9 shows another example of emission spectra of illumination light by the white illumination light source, the special light source and the fluorescent material. As shown, depending on types of the fluorescent materials, the fluorescent material is excited by not only the blue laser light having the wavelength of 445 nm but also the purple laser light having the wavelength of 405 nm. In this case, when the light amount of the purple laser light having the wavelength of 405 nm is increased, the state that the entire observation image is bluish can be mitigated by the excitation light of the fluorescent material caused by the purple laser light, so that it is possible to suppress the change in color balance of the white illumination. In the meantime, an excitation light emission amount of the fluorescent material by the purple laser light is set to be one-several-th (at least ⅓, preferably ⅕, more preferably 1/10 or less) of an excitation light emission amount by the blue laser light. In this manner, by suppressing the excited emission light of the fluorescent material by the purple laser light, it is possible to perform the special light observation while properly keeping the color temperature of the white illumination.

Figure 10:
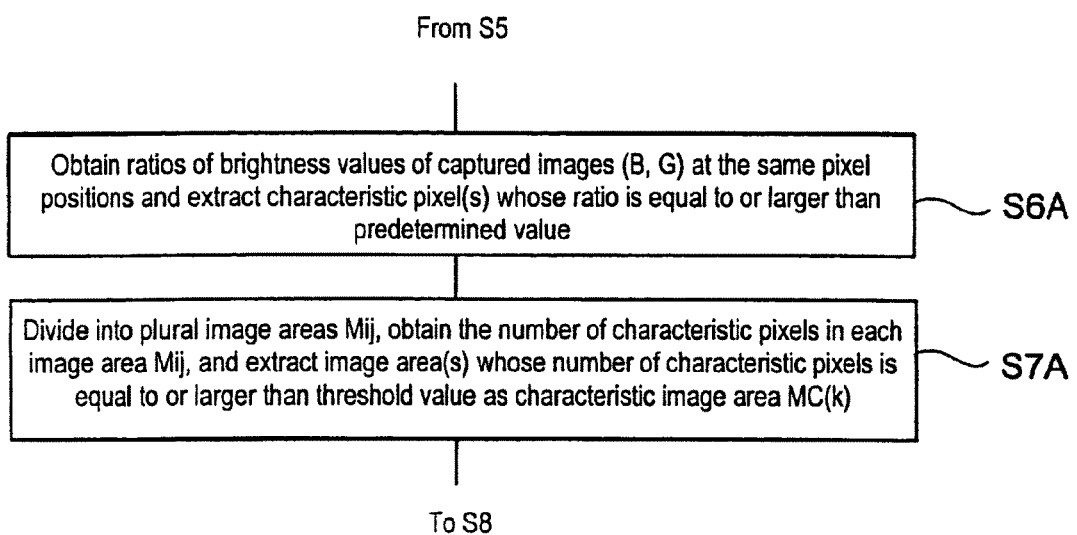
FIG. 10 is a flow chart showing alternative sequences of S6 and S7 in FIG. 6.

In the meantime, the extraction of the characteristic image area MC(k) may be performed as follows. That is, the characteristic image area(s) MC(k) are extracted by comparing the brightness values of the captured images (B, G) in divided image area units of the captured images (B, G). However, when comparing the brightness values of the captured images (B, G) in pixel units of each captured image, it is possible to extract an object to be emphasized by the narrow-band light more accurately. More specifically, as shown in FIG. 10 illustrating alternative sequences of S6 and S7 of FIG. 6, a ratio of a brightness value of the captured image (B), which includes much information of reflection light of the narrow-band light having the center wavelength of 405 nm, to a brightness value of the captured image (G) at the same pixel position is calculated, and a characteristic pixel(s) in which the ratio is equal to or greater than a predetermined ratio are extracted (S6A).

As shown in FIG. 7B, the captured image (B) and the captured image (G) are commonly divided into the image areas Mij, and the number of extracted characteristic pixels is calculated for each of the image areas Mij. Then, an image area(s) in which the number of characteristic pixels is equal to or greater than a predetermined threshold value are extracted as the characteristic image area(s) MC(k) (S7A).

In this manner, by comparing the brightness values of the captured images (B, G) in pixel units at the same pixel positions, it is possible to extract the body information, which is obtained by the narrow-band light, more certainly.

Next, another exemplary embodiment of the endoscope will be described.

Figure 11:
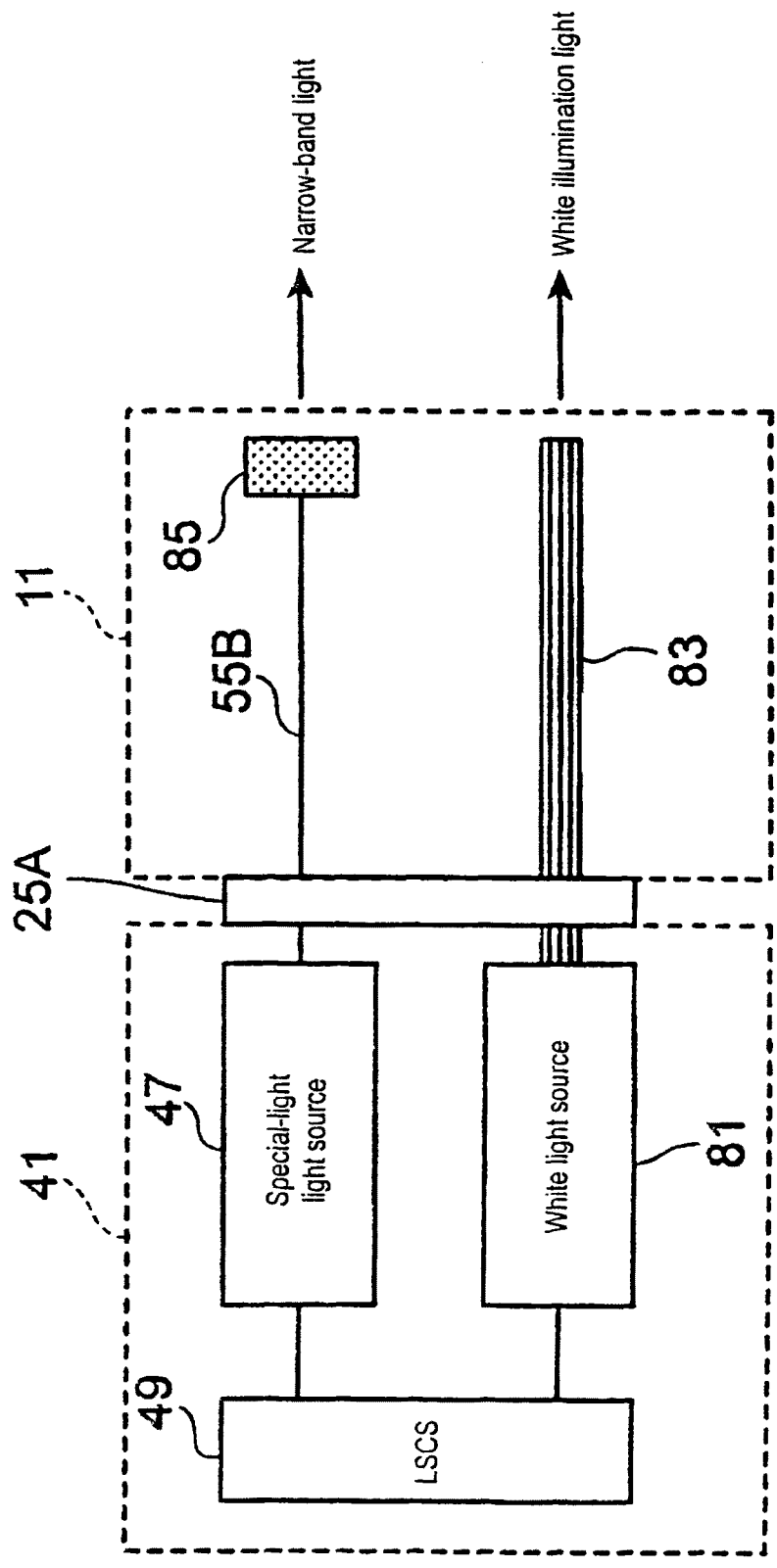
FIG. 11 shows a schematic structure of another endoscope in which a white light source is modified.

FIG. 11 shows a schematic structure of another endoscope in which the white light source is modified. In the structure shown in FIG. 11, as a white light source 81, a light source, which emits light of a broad wavelength band, such as a halogen lamp, a xenon lamp or a white light emitting diode, is used to emit the white illumination light from the leading end of the endoscope 11 through a light guide 83 that is an optical fiber bundle. The light emitted from the special-light light source 47 is transmitted to the leading end of the endoscope 11 through the connector section 25A by the optical fiber 55B, as described above. Then, the light is provided as narrow-band light from a light deflection/diffusion member 85 that is disposed at a light emitting end of the optical fiber 55B. In the meantime, the light deflection/diffusion member 85 may be replaced with a light irradiation window that is disposed at the leading end of the endoscope 11.

With the above structure, it is possible to introduce the white illumination light having high color rendering properties and having a broad spectrum characteristic with a simple structure. Furthermore, it is possible to suppress the heat generation of the leading end of the endoscope. In addition, since it is possible to completely separate and emit the white illumination light and the narrow-band light, it is possible to emit the narrow-band light to a region to be observed without a fluorescent material. Therefore, it is possible to remove the unnecessary light emission from the fluorescent material, so that it is possible to easily control the light amount.

Figure 12:
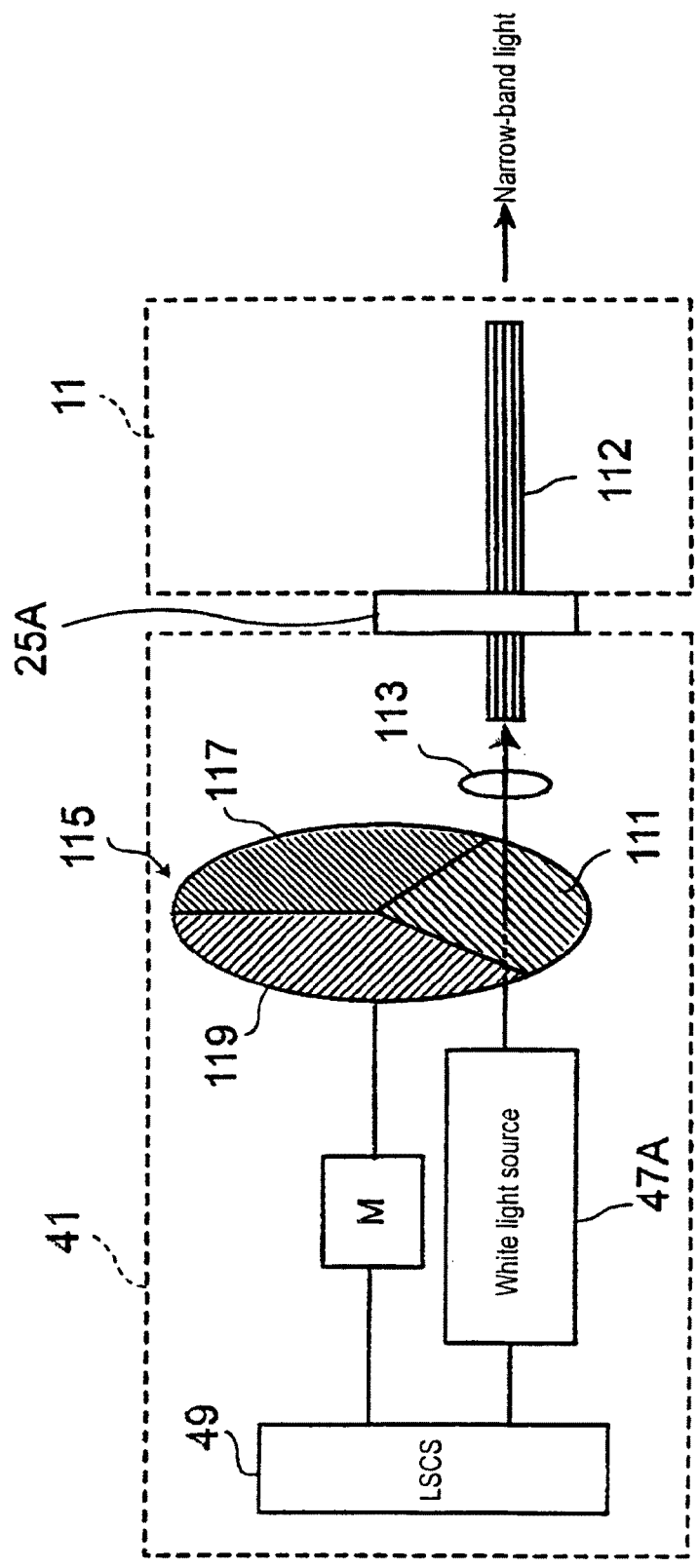
FIG. 12 shows a schematic structure of further another endoscope using a white light source and a laser light source.

FIG. 12 shows a schematic structure of further another endoscope in which the structure of the special light source is modified. In FIG. 12, the optical system of the white illumination light is omitted, and any structure shown in FIG. 1 or FIG. 11 may be used. The special light source of this structure generates the narrow-band light by (i) a white light source 47A, which emits light of a broad wavelength band such as a halogen lamp, a xenon lamp or a white light emitting diode, in place of the purple laser light source 47 emitting the narrow-band light, and (ii) optical filter 111. The transmitted light from the optical filter 111 is introduced into a light incident end of a light guide 112 by a light collection member 113 and is guided to the leading end of the endoscope 11 by the light guide 112.

The optical filter 111 is a narrow band-pass filter that allows only a predetermined narrow-band wavelength component of incident white light to pass therethrough and is formed in a part of a rotation filter plate 115. The rotation filter plate 115 can switch among the optical filters 111, which are disposed in the middle of a light path of the white light, through rotation driving by a motor M. That is, plural optical filters 111, 117, 119 (the number of optical filters is not limited to three) are disposed in the middle of the light path so as to be switched and thus, so that the narrow-band lights of different types can be emitted.

With the above structure, it is possible to simply generate any narrow-band light from the white light source.

The invention is not limited to the above exemplary embodiments. In other words, the exemplary embodiments can be changed and/or modified by one skilled in the art based on the specification and the well-known technology, which are within the scope of the invention to be protected.

As described above, one embodiment of the invention discloses the following matters.

(1) A method controls an amount of illumination light of an endoscope. The endoscope includes a first light source, a second light source and an imaging section. The first light source emits white illumination light. The second light source that emits narrow-band light having a wavelength band narrower than that of the white illumination light. The imaging section images a region to be observed by an imaging device having a plurality of detection pixels. The method includes: causing the imaging section to output a captured image signal including both of a return light component of the white illumination light from the region to be observed and a return light component of the narrow-band light from the region to be observed; and selectively extracting the return light component of the narrow-band light from the captured image signal; and changing an amount of the narrow-band light emitted from the second light source to change a brightness level of the extracted return light component of the narrow-band light.

With the method of controlling the endoscope, when observation is performed using the white illumination light from the first light source and the narrow-band light from the second light source as the illumination light, it is possible to always obtain the observation information by the narrow-band light having the proper brightness level even when the observation conditions such as an observation object and an observation position are changed. Thereby, the information obtained by the narrow-band light can be clearly observed without being hidden by the white illumination light.

(2) In the method of (1), a center wavelength of the narrow-band light emitted from the second light source may be in a range of 360 nm to 470 nm.

With the method of controlling the endoscope, the center wavelength of the second light source is within the range of 360 nm to 470 nm. Therefore, it is possible to clearly detect the image information indicating the superficial blood vessels or microstructure of the body tissue, particularly.

(3) The method of any one of (1) to (2) may further include: generating captured images of plural reference colors based on the captured image signal, wherein the captured images include a first captured image and a second captured image, and of the captured images, the first captured image contains the most return light component of the narrow-band light emitted from the second light source; and dividing the first captured image and the second captured image, which has a different reference color from that of the first captured image, into common plural image areas; integrating brightness values in each image area of the first captured image to calculate an integrated brightness value of each image area of the first captured image; integrating brightness values in each image area of the second captured image to calculate an integrated brightness value of each image area of the second captured image; obtaining a ratio of (i) the integrated brightness value of each image area of the first captured image and (ii) the integrated brightness value of the image area, having a same image positional relationship with each image area of the first captured image, of the second captured image; extracting image areas, of the first and second captured images, whose ratio is equal to or larger than a threshold value, as characteristic image areas; and changing the amount of light emitted from the second light source while adopting a brightness level of the extracted characteristic image area of the first captured image as a brightness level of the return light component of the narrow-band light from the region to be observed.

With the method of controlling the endoscope, among the image areas obtained by dividing the captured images, the emission light amount of the second light source is changed so that the return light component of the narrow-band light has a desired brightness level in the characteristic image area in which a ratio of the integrated brightness values of the different reference colors is equal to or greater than the predetermined threshold value. Thereby, it is possible to particularly emphasize and observe the body information in the image areas where the body information obtained by the narrow-band light is much included.

(4) The method of any one of (1) to (2) may further include: generating captured images of plural reference colors based on the captured image signal, wherein the captured images include a first captured image and a second captured image, and of the captured images, the first captured image contains the most return light component of the narrow-band light emitted from the second light source; and dividing the first captured image and the second captured image, which has a different reference color from that of the first captured image, into common plural image areas; obtaining a ratio of (i) a brightness value of each image pixel of the first captured image and (ii) a brightness value of a pixel, having a same image positional relationship with each pixel of the first captured image, of the second captured image; extracting pixels, of the first and second captured images, whose ratio is equal to or larger than a threshold value, as characteristic pixels; obtaining the number of characteristic pixels in each image area of the first and second captured images; extracting image areas, of the first and second captured images, whose number of characteristic pixels is equal to or larger than a threshold value, as characteristic image areas; and changing the amount of light emitted from the second light source while adopting a brightness level of the extracted characteristic image area of the first captured image as a brightness level of the return light component of the narrow-band light from the region to be observed.

With the method of controlling the endoscope, the characteristic pixels whose ratio of the brightness values of the different reference colors at the same pixel position is equal to or greater than the predetermined ratio are extracted. Among the image areas obtained by dividing the captured images, the emission light amount of the second light source unit is changed so that the light receiving component of the narrow-band light has a desired brightness level in the characteristic image area where the number of the characteristic pixels is equal to or greater than the predetermined threshold value. Thereby, it is possible to particularly emphasize and observe the body information in the image area in which the body information obtained by the narrow-band light is much included.

(5) In the method of any one of (1) to (4), if the return light component of the white illumination light from the region to be observed and the return light component of the narrow-band light from the region to be observed exceed a predetermined target brightness level after the amount of light emitted from the second light source is changed, the amount of light emitted from the first light source and the amount of light emitted from the second light source may be decreased.

With the method of controlling the endoscope, even when the brightness level of the return light components exceeds the target brightness level after the emission light amount of the second light source is changed, it is possible to correct the return light to have a proper brightness level without changing the balance of the lights emitted from the first light source and the second light source.

(6) In The method of any one of (3) to (5), light components of colors detected by the imaging device may include light components of a primary color system of blue, green and red. The reference color of the first captured image may be blue. The reference color of the second captured image may be green.

With the method of controlling the endoscope, it is possible to observe the body information obtained by the irradiation of the narrow-band light of the blue wavelength, more clearly from the detection result of the reference color light of the primary color system.

(7) In the method of any one of (3) to (5), light components of color detected by the imaging device may include light components of a complementary color system including magenta, cyan and yellow. The light components of the detected colors may be converted into light components of a primary color system of blue, green and red. The reference color of the first captured image may be the converted blue. The reference color of the second captured image may be the converted green.

With the method of controlling the endoscope, it is possible to observe the body information obtained by the irradiation of the narrow-band light of the blue wavelength, more clearly from the detection result of the reference color light of the complementary color system.

(8) A method of controlling an endoscope includes switching between (i) a special light observation mode in which the method of any one of (1) to (7) is performed, and (ii) a normal observation mode in which brightness levels of the plural captured images are changed at a same ratio.

With the method of controlling the endoscope, the special light observation mode and the normal observation mode can be selectively switched, so that the usability of the endoscope can be improved.

(9) An endoscope includes a first light source, a second light source, an imaging section and a controller. The first light source emits white illumination light. The second light source emits narrow-band light of a wavelength band narrower than the white illumination light. The imaging section includes an imaging device having a plurality of detection pixels. The imaging section outputs a captured image signal. The controller changes an amount of light emitted from the second light source, based on the control method of any one of (1) to (8).

With the endoscope, when the observation is performed using the illumination light having the white light added to the narrow-band light, it is possible to always obtain the observation information by the narrow-band light having the proper brightness level even when the observation conditions such as an observation object and an observation position are changed. Thereby, the information obtained by the narrow-band light can be clearly observed without being hidden by the white illumination light.

(10) In the endoscope of (9), the first light source may include a fluorescent material, and a semiconductor light emitting device that emits excitation light of the fluorescent material.

With the endoscope, the white illumination light is formed by light emitted from the semiconductor light emitting device and the excitation emission light from the fluorescent material by the light emission. Therefore, the white light having a high intensity is obtained in a high light emission efficiency, and the intensity of the white light can be easily adjusted. Also, the semiconductor light emitting device is used, so that the change in color temperature and chromaticity of the white light can be suppressed.

(11) In the endoscope of (9), the first light source may emit light which originates from a xenon light source or a halogen light source.

With the endoscope, the white light of a broad spectrum is obtained from the xenon light source or halogen light source, so that it is possible to improve the color rendering properties.

(12) In the endoscope of any one of (9) to (11), the second light source may include a semiconductor light emitting device.

With the endoscope, the semiconductor light emitting device is used to emit the narrow-band light of high efficiency and high intensity.

(13) In the endoscope of any one of (9) to (11), the second light source may generate the narrow-band light by having light originating from a xenon light source or a halogen light source pass through a narrow-band pass filter which only allows to pass light having predetermined narrow-band wavelength components therethrough. The second light source may emit the generated narrow-band light.

With the endoscope, it is possible to simply generate desired narrow-band light by the narrow band-pass filter.

What is claimed is:

1. A method of controlling an endoscope comprising a first light source section that emits white illumination light, a second light source section that emits narrow-band light having a wavelength band narrower than that of the white illumination light, and an imaging section that captures a region to be observed by an imaging device comprising detection pixels of plural colors, the method comprising:
   causing the imaging section to output a captured image signal including a return light component of the white illumination light from the region to be observed and a return light component of the narrow-band light from the region to be observed, wherein the captured image signal comprises a red image signal, a green image signal, and a blue image signal;
   generating captured images of red, green, and blue colors based on the red, green, and blue image signals, respectively, wherein the captured images include a first captured image, and of the captured images, the first captured image contains a most return light component of the narrow-band light emitted from the second light source;
   changing a brightness level of the first captured image relatively to brightness levels of captured images based on the red and green signals;
   dividing the first captured image and a second captured image which has a different reference color from that of the first captured image into common plural image areas;
   integrating brightness values in each image area of the first captured image to obtain an integrated brightness value of each image area of the first captured image;
   integrating brightness values in each image area of the second captured image to obtain an integrated brightness value of each image area of the second captured image;
   obtaining a ratio of the integrated brightness value of each image area of the first captured image and the integrated brightness value of the image area, having a same image positional relationship with each image area of the first captured image, of the second captured image;
   extracting image areas, of the first and second captured images, whose ratio is equal to or larger than a threshold value, as characteristic image areas; and
   selectively changing a brightness level of the characteristic image area of the first captured image.

2. The method according to claim 1, wherein a center wavelength of the narrow-band light emitted from the second light source is in a range of 360 nm to 470 nm.

3. The method according to claim 1, wherein the changing of the brightness level includes changing a correction matrix which is used to correct brightness values of respective pixels in the captured image signal by a matrix operation,
   the method further comprising:
   correcting a captured image signal, which is newly obtained from the imaging section, using the changed correction matrix.

4. The method according to claim 3, further comprising:
   if a brightness level of an image obtained by correcting the captured image signal, which is newly obtained from the imaging section, using the changed correction matrix exceeds a predetermined target brightness level, resetting the correction matrix so as to decrease the brightness level of the corrected image.

5. The method according to claim 1, wherein light components of detection colors which are detected by the imaging device include light components of a primary color system containing blue, green and red,
   wherein the reference color of the first captured image comprises blue, and
   wherein the reference color of the second captured image comprises green.

6. The method according to claim 1, wherein light components of detection colors which are detected by the imaging device include light components of a complementary color system containing magenta, cyan, and yellow, wherein the light components of the respective detection colors are converted into light components of a primary color system of blue, green and red, wherein the reference color of the first captured image comprises blue, and wherein the reference color of the second captured image comprises green.

7. The method according to claim 1, wherein the imaging device includes a CCD-type (Charge Coupled Device type) image sensor.

8. The method according to claim 1, wherein the imaging device includes a CCD-type (Charge Coupled Device type) image sensor, and wherein the brightness level of the first captured image is changed by changing an amplification ratio of an amplifier of each pixel of the imaging device.

9. A method of controlling an endoscope, said method comprising:

switching between:
a special light observation mode in which the method according to claim 1 is performed; and
a normal observation mode in which brightness levels of the plural captured images are changed at a same ratio.

10. A method of controlling an endoscope comprising a first light source section that emits white illumination light, a second light source section that emits narrow-band light having a wavelength band narrower than that of the white illumination light, and an imaging section that captures a region to be observed by an imaging device comprising detection pixels of plural colors, the method comprising:

causing the imaging section to output a captured image signal including a return light component of the white illumination light from the region to be observed and a return light component of the narrow-band light from the region to be observed, wherein the captured image signal comprises a red image signal, a green image signal, and a blue image signal;

generating captured images of red, green, and blue colors based on the red, green, and blue image signals, respectively, wherein the captured images include a first captured image, and of the captured images, the first captured image contains a most return light component of the narrow-band light emitted from the second light source;

changing a brightness level of the first captured image relatively to brightness levels of captured images based on the red and green signals;

dividing the first captured image and a second captured image which has a different reference color from that of the first captured image into common plural image areas;

obtaining a ratio of a brightness value of each image pixel of the first captured image and a brightness value of a pixel, having a same image positional relationship with each pixel of the first captured image, of the second captured image;

extracting pixels, of the first and second captured images, whose ratio is equal to or larger than a threshold value, as characteristic pixels;

obtaining a number of characteristic pixels in each image area of the first and second captured images;

extracting image areas, of the first and second captured images, whose number of characteristic pixels is equal to or larger than a threshold value, as characteristic image areas; and selectively changing a brightness level of the characteristic image area of the first captured image.

11. An endoscope, comprising:
a first light source section that emits white illumination light;
a second light source section that emits narrow-band light having a wavelength band narrower than that of the white illumination light;
an imaging section that captures a region to be observed by an imaging device having detection pixels of plural colors; and
a control section,
wherein the control section causes the imaging section to output a captured image signal including a return light component of the white illumination light from the region to be observed and a return light component of the narrow-band light from the region to be observed, wherein the captured image signal comprises a red image signal, a green image signal, and a blue image signal,
wherein the control section generates captured images of red, green, and blue colors based on the red, green, and blue image signals, respectively,
wherein the captured images include a first captured image, of the captured images, the first captured image contains a most return light component of the narrow-band light emitted from the second light source, and
wherein the control section changes a brightness level of the first captured image relatively to brightness levels of captured images based on the red and green signals;
a divider for dividing the first captured image and a second captured image which has a different reference color from that of the first captured image into common plural image areas;
an integrator for integrating brightness values in each image area of the first captured image to obtain an integrated brightness value of each image area of the first captured image, and for integrating brightness values in each image area of the second captured image to obtain an integrated brightness value of each image area of the second captured image;
a unit for obtaining a ratio of the integrated brightness value of each image area of the first captured image and the integrated brightness value of the image area, having a same image positional relationship with each image area of the first captured image, of the second captured image;
an extractor for extracting image areas, of the first and second captured images, whose ratio is equal to or larger than a threshold value, as characteristic image areas; and
a selector for selectively changing a brightness level of the characteristic image area of the first captured image.

12. The endoscope according to claim 11, wherein the first light source section includes:
a phosphor; and
a semiconductor light emitting element that emits excitation light for the phosphor.

13. The endoscope according to claim 11, wherein the first light source section emits light which originates from a xenon light source or a halogen light source.

14. The endoscope according to claim 11, wherein the second light source section includes a semiconductor light emitting element.

15. The endoscope according to claim 11, wherein the second light source section generates the narrow-band light by having light originating from a xenon light source or a halogen light source pass through a narrow-band pass filter which only allows to pass light having predetermined narrow-band wavelength components therethrough; and
    wherein the second light source section emits the generated narrow-band light.

16. An endoscope, comprising:
- a first light source section that emits white illumination light;
- a second light source section that emits narrow-band light having a wavelength band narrower than that of the white illumination light;
- an imaging section that captures a region to be observed by an imaging device having detection pixels of plural colors; and
- a control section,
  - wherein the control section causes the imaging section to output a captured image signal including a return light component of the white illumination light from the region to be observed and a return light component of the narrow-band light from the region to be observed, wherein the captured image signal comprises a red image signal, a green image signal, and a blue image signal,
  - wherein the control section generates captured images of red, green, and blue colors based on the red, green, and blue image signals, respectively,
  - wherein the captured images include a first captured image, of the captured images, the first captured image contains a most return light component of the narrow-band light emitted from the second light source, and
  - wherein the control section changes a brightness level of the first captured image relatively to brightness levels of captured images based on the red and green signals;
- a divider for dividing the first captured image and a second captured image which has a different reference color from that of the first captured image into common plural image areas;
- a unit for obtaining a ratio of a brightness value of each image pixel of the first captured image and a brightness value of a pixel, having a same image positional relationship with each pixel of the first captured image, of the second captured image;
- an extractor for extracting pixels, of the first and second captured images, whose ratio is equal to or larger than a threshold value, as characteristic pixels;
- a unit for obtaining a number of characteristic pixels in each image area of the first and second captured images;
- a unit for extracting image areas, of the first and second captured images, whose number of characteristic pixels is equal to or larger than a threshold value, as characteristic image areas; and
- a selector for selectively changing a brightness level of the characteristic image area of the first captured image.

17. An endoscope, comprising:
- a first light source section that emits white illumination light;
- a second light source section that emits narrow-band light having a wavelength band narrower than that of the white illumination light;
- an imaging section that captures a region to be observed by an imaging device having detection pixels of plural colors; and
- a control section,
  - wherein the control section causes the imaging section to output a captured image signal including a return light component of the white illumination light from the region to be observed and a return light component of the narrow-band light from the region to be observed, wherein the captured image signal comprises a red image signal, a green image signal, and a blue image signal,
  - wherein the control section generates captured images of red, green, and blue colors based on the red, green, and blue image signals, respectively,
  - wherein the captured images include a first captured image, of the captured images, the first captured image contains a most return light component of the narrow-band light emitted from the second light source, and
  - wherein the control section changes a brightness level of the first captured image relatively to brightness levels of captured images based on the red and green signals;
- a divider for dividing the first captured image and a second captured image which has a different reference color from that of the first captured image into common plural image areas; and
- an integrator for integrating brightness values in each image area of the first captured image to obtain an integrated brightness value of each image area of the first captured image, and for integrating brightness values in each image area of the second captured image to obtain an integrated brightness value of each image area of the second captured image.

18. The endoscope according to claim 17, further comprising:
- a unit for obtaining a ratio of the integrated brightness value of each image area of the first captured image and the integrated brightness value of the image area, having a same image positional relationship with each image area of the first captured image, of the second captured image; and
- an extractor for extracting image areas, of the first and second captured images, whose ratio is equal to or larger than a threshold value, as characteristic image areas.

* * * * *